United States Patent [19]
Zantos

[11] Patent Number: 5,913,814
[45] Date of Patent: Jun. 22, 1999

[54] METHOD AND APPARATUS FOR DEFLATION OF AN INTRA-AORTIC BALLOON

[75] Inventor: George N. Zantos, Woburn, Mass.

[73] Assignee: Belmont Instrument Corporation, Billerica, Mass.

[21] Appl. No.: 08/922,149

[22] Filed: Aug. 26, 1997

[51] Int. Cl.$^6$ ................................................... A61M 1/10
[52] U.S. Cl. ................................................................. 600/18
[58] Field of Search .......................... 600/16–18; 623/3; 604/96–99

[56] References Cited

U.S. PATENT DOCUMENTS

4,794,910  1/1989  Mushika .................................... 600/18
5,158,529  10/1992  Kanai .
5,413,549  5/1995  Leschinsky .
5,817,001  10/1998  Leschinsky et al. ....................... 600/18

Primary Examiner—Jeffrey R. Jastrzab
Attorney, Agent, or Firm—Morse & Altman

[57] ABSTRACT

A method for decreasing the deflation time of an intra-aortic balloon comprises removing a portion of the gas from the closed pneumatic system during balloon inflation and then restoring the removed gas to the system at or near the end of balloon deflation. An apparatus for decreasing the deflation time of an intra-aortic balloon comprises an auxiliary chamber connected by an auxiliary valve to the pneumatic system near the volume chamber. The auxiliary valve is controlled to open and close the auxiliary chamber to the pneumatic system at predetermine points in the balloon inflation/deflation cycle. Removing a portion of the gas from the pneumatic system increases the pressure gradient from the balloon to the volume chamber, increasing the gas flow from the balloon, and decreasing deflation time.

16 Claims, 4 Drawing Sheets

METHOD AND APPARATUS FOR DEFLATION OF AN INTRA-AORTIC BALLOON

BACKGROUND OF THE INVENTION

1. Field of the Invention

The present invention relates to cardiac assist devices, and more specifically, to intra-aortic balloon pumps and a method and apparatus for reducing the deflation time of the intra-aortic balloon.

2. The Prior Art

Intra-aortic balloon counterpulsation, or pumping (IAEP), is the most widely used type of cardiac assist, with more than 150,000 procedures per year world-wide. It is used to augment the pumping action of the heart in conjunction with open heart surgery or severe heart failure. An IABP consists generally of a catheter with a long narrow balloon at one end and a volume displacement pump at the other. The balloon is inserted into the femoral artery in the leg, and up the arterial tree into the descending aorta, the large artery coming directly from the heart. The volume displacement pump inflates and deflates the balloon once every heart beat at exact points in the cardiac cycle by shuttling a gas into and out of the balloon. The balloon is inflated just after the aortic valve closes and deflates just prior to the next beat. The IABP is generally in place for two to three days. However, in cases of severe heart failure and with no alternate treatment available, a few patients have remained on the device for long periods, up to several months.

The IABP augments the failing heart by two mechanisms. First, it increases blood flow to the coronary arteries which feed the heart itself. The balloon inflates just as the heart completes the blood ejection portion of its cycle and the aortic valve closes. The increased pressure caused by the balloon displacement pushes blood into the coronary arteries. Second, blood displaced by the inflating balloon augments the pressure from the heart to push blood forward out of the aorta. Just before the next blood ejection portion of the cycle, the balloon is deflated, reducing aortic blood pressure so that blood refills the volume of the aorta taken up by the previously inflated balloon at lower pressure, reducing the work load of the heart.

An IABP of the prior art includes a control system and a pneumatic system. The control system causes the balloon to inflate and deflate synchronously with the heart, while monitoring and displaying various parameters concerning the procedure. The control system has seven major functions. 1) It acquires, amplifies, and displays the patient's electrocardiogram (ECG), arterial pressure (AP), and heart rate measurements. (2) It acquires a synchronizing signal from the heart. Usually the ECG R-wave is used, but sometimes the upstroke of arterial pressure is used. (3) It monitors the acquired signals and alerts the operator if the signals are noisy or lost. (4) It provides a means for the operator to set inflation and deflation timing with reference to the AP waveform displayed on the pump monitor. (5) It inflates and deflates the balloon according to the operator settings and meters the correct volume of gas into the balloon so that it fully inflates but does not overinflate. (6) It monitors and displays the balloon gas pressure, analyzes the pressure waveform for unsafe conditions, e.g., gas leakage, kinked line, disconnected balloon, etc., and alerts the operator to these conditions. (7) It analyzes and compensates for irregular cardiac rhythms by adjusting the inflate/deflate timing appropriately.

Figure 1:
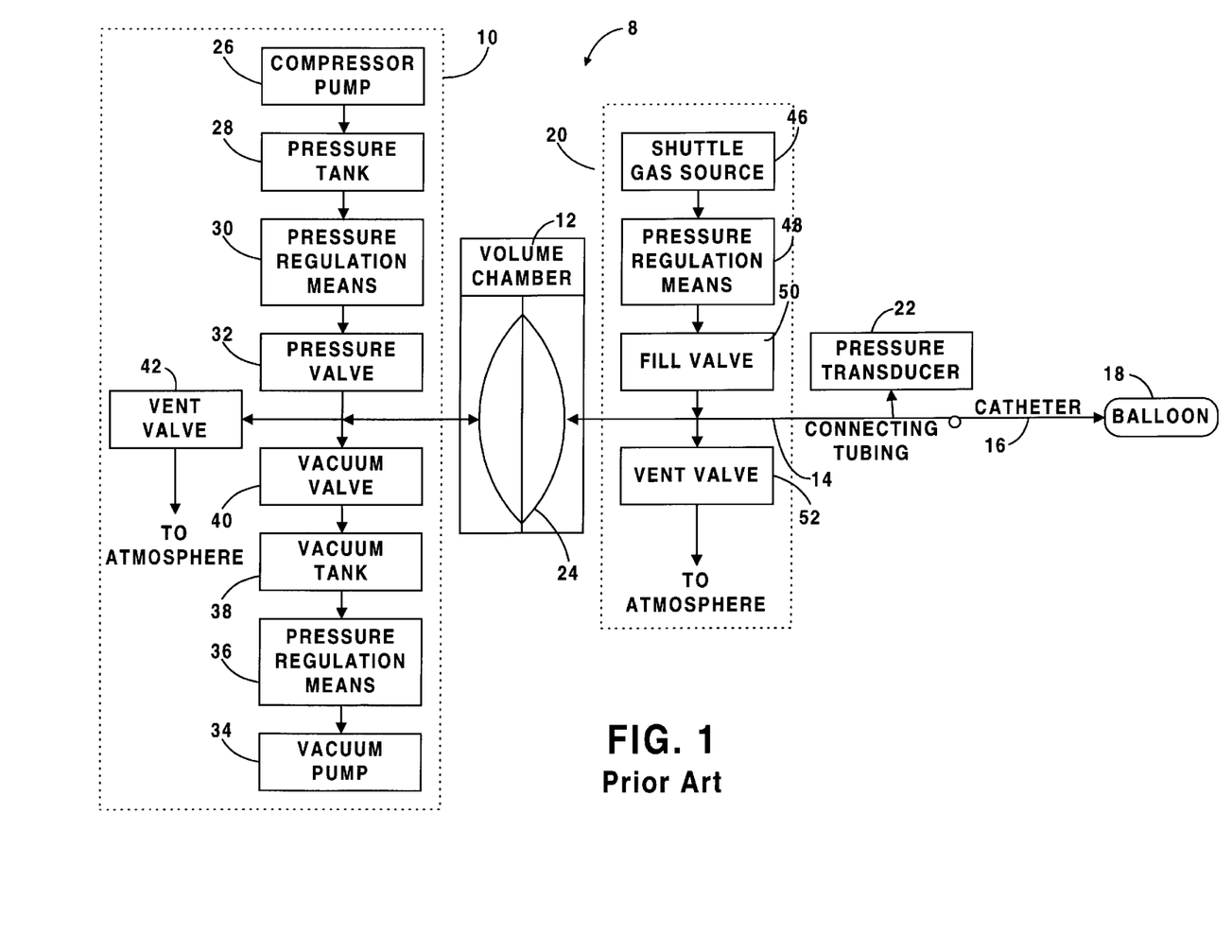
FIG. 1 shows a block diagram of a prior art intra-aortic balloon pump system.

The pneumatic system 8, shown in FIG. 1, consists of a drive 10, volume chamber 12, connecting tubing 14, catheter 16, balloon 18, shuttle gas supply 20, and pressure transducer 22. The drive 10 supplies force to inflate and deflate the balloon by moving a diaphragm 24 in the volume chamber 12 forward during inflation and backward during deflation. The drive 10 may consist of a compressor 26 and a vacuum pump 34 which produces drive pressure and vacuum for moving the diaphragm 24. In this configuration, reservoir tanks 28, 36 and a pressure regulation means 30, 38 are used to control the pressure and vacuum. Valves 32, 40 are used to apply the pressure and vacuum respectively during appropriate parts of the cardiac cycle. Sometimes a third valve 42 is used to vent the pressure prior to applying vacuum. Another type of drive uses a motor to produce a linear displacement of the volume chamber diaphragm to actuate inflation and deflation.

The volume chamber 12 controls the pumped volume of the balloon 18. It includes the diaphragm 24 that separates the drive from the shuttle gas and that moves the shuttle gas into and out of the balloon 18. The diaphragm 24 may be a flexible polymer elastomer driven by gas/vacuum, a rigid plate or piston driven by a motor, or other configuration. The connecting tubing 14 is a series of tubes that interconnect the volume chamber 12, shuttle gas supply 20, pressure transducer 22, and catheter 16. The catheter 16 is small bore tube that connects the balloon 18 to the remainder of the system 8 and runs primarily within the body. The pressure transducer 22 for monitoring gas pressure taps off of the connecting tubing 14 adjacent to the volume chamber 12. The typical balloon 18 is generally cylindrical with a long, narrow shape. The expanding outer surface does not stretch, but maintains a constant volume once inflated.

The shuttle gas supply 20 provides the gas that inflates the balloon. It includes a gas source 46 (usually a portable tank), a reducing pressure regulator means 48 to reduce the source pressure to a safe level, and valves 50, 52 for filling and venting gas from the system at the connecting tubing 14. Generally, the shuttle gas supply 20 also includes a tank pressure gauge and a blow-off valve to vent gas if the pressure exceeds a safe level.

Helium is the gas of choice. The catheter 16 is necessarily narrow so that it does not significantly interfere with blood flow in the arterial tree between the femoral artery and the aorta. Consequently, the catheter bore is very small. Helium, the smallest molecular weight, non-flammable gas, flows the quickest through the small bore, optimizing the inflation and deflation rate of the balloon 18.

The IABP is a closed system in which a fixed volume of gas is shuttled between the volume chamber 12 and the balloon 18 through the connecting tubing 14 and catheter 16. The diaphragm 24, powered by the drive 10, moves rapidly forward to provide the forward force to push the gas from the volume chamber 12. At deflation the operation is reversed: the diaphragm 24 moves rapidly backward, creating a partial vacuum in the volume chamber 12, pulling gas from the balloon 18 into the volume chamber 12. In this process, the rate of inflation or deflation is primarily determined by the pressure difference across the tubing 14 and catheter 16, the difference between the pressure in the balloon 18 and the pressure in the volume chamber 12. During deflation, the pressure in the balloon 18 is the AP, the pressure put on the balloon 18 by the blood in the aorta. During deflation, the pressure in the volume chamber 12 starts as a partial vacuum and rises to the pressure to which the volume chamber 12 was initially filled as gas flows from the balloon 18 to the volume chamber 12 as the balloon 18 deflates.

One measure of IABP performance is the rate at which the balloon 18 inflates and deflates. This performance is important when the heart rate is high or the cardiac rhythm is irregular. The deflate rate is particularly important in the case of an early beat in an arrhythmia situation. If the balloon 18 does not deflate before the heart begins its ejection cycle, the aortic blockage caused by the inflated balloon 18 puts an additional strain on what is already a weakened heart.

One prior art strategy for improving deflation time is to initially fill the gas system to a pressure lower than the ambient (atmospheric) pressure, so that there is a partial vacuum at full deflation and a strong pressure gradient remains across the catheter. Maintaining a partial vacuum throughout the entire deflated period, typically a substantial fraction of the heart interval, especially at high heart rates, has several drawbacks. If there should be a leak in the balloon, blood can be pulled into the system. If there should be a leak in the internal connections or connecting tubing, air can be pulled into the system. Also, leaks are more difficult to detect. The presence of a leak or of overfilling is determined by monitoring the gas pressure after complete deflation. When the deflated pressure is below ambient and the inflated pressure is above ambient, a leak will cause a gas gain at deflation and a gas loss at inflation, in effect, partially canceling each other out and making a leak much more difficult to detect. If the pressures during both inflation and deflation are above ambient, a leak will cause a loss when averaged over the entire cycle.

Thus, it is preferable to operate the system with a steady-state deflation pressure at or just above ambient. It is easier to do the initial fill and it is possible to operate in an emergency when no gas is available by breaking the closed system briefly and initializing from atmospheric pressure directly.

SUMMARY OF THE INVENTION

An object of the present invention is to provide a method for rapid deflation of an intra-aortic balloon.

Another object is to provide a method for rapid deflation of an intra-aortic balloon that utilizes internal deflated pressures at or above atmospheric pressure.

A further object is to provide an apparatus that provides for rapid deflation of an intra-aortic balloon.

The present invention includes a method for decreasing the deflation time of the intra-aortic balloon while using a fill pressure at or slightly above atmospheric pressure, rather than the below atmospheric pressure used in IABPs of the prior art to augment the deflation rate, as described above. The decreased inflation time is achieved by increasing the gradient across the tubing and catheter over that of the prior art during the deflation time. This is accomplished by removing a portion of the gas from the pneumatic system during balloon inflation and then restoring it to the system at or near the end of balloon deflation.

Just before or during balloon inflation, an auxiliary chamber is opened to the pneumatic system so that a portion of the gas from the system flows into the chamber. At a particular point during balloon inflation, the chamber is closed to the system, removing the gas in the auxiliary chamber from the system. The auxiliary chamber remains closed during the time that the balloon is inflated and during balloon deflation. By removing a portion of the gas from the pneumatic system, the pressure gradient from the balloon to the volume chamber is increased over the prior art, increasing the gas flow from the balloon, and decreasing deflation time. This works because the system is closed, that is, the amount of gas in the system, including the auxiliary chamber, does not change after it has been initially filled. After the balloon is deflated, the auxiliary chamber is opened to the system to readmit the gas.

Other objects of the present invention will become apparent in light of the following drawings and detailed description of the invention.

BRIEF DESCRIPTION OF THE DRAWINGS

For a fuller understanding of the nature and object of the present invention, reference is made to the accompanying drawings, wherein.

DETAILED DESCRIPTION

Figure 2:
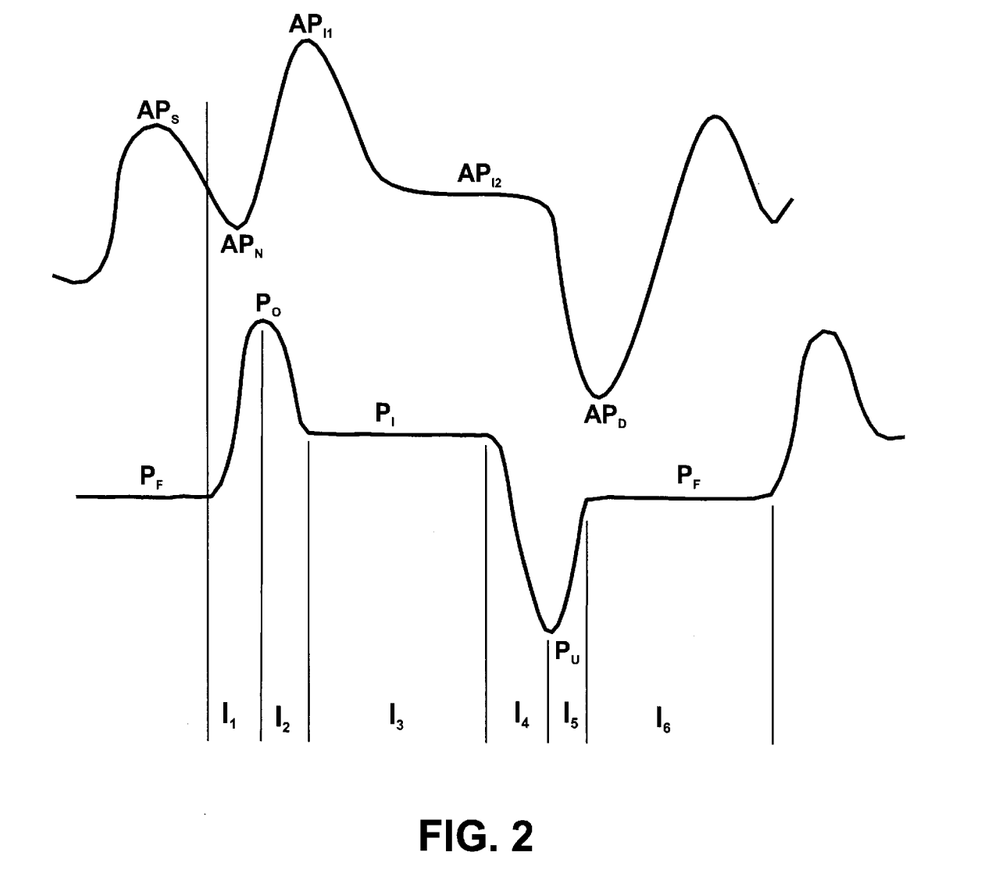
FIG. 2 shows a graph of gas pressure and arterial pressure versus time for an IABP of the prior art.

Before details of the present invention are presented, a discussion of the operational cycle of an IAPB of the prior art is in order. Gas pressure and AP versus time in a system of the prior art are shown in FIG. 2, where the gas pressure is measured at the outlet of the volume chamber 12 and the AP is measured at the balloon 18. Prior to the beginning of the cycle, the balloon 18 is deflated and the gas pressure is at a steady-state level $P_F$, the initial pressure to which the system is filled. Interval $I_1$ begins when the controller anticipates the end of systole, the "dichrotic notch" at $AP_N$ in the AP waveform after $AP_S$, and the controller causes the volume chamber diaphragm 24 to move forward rapidly, sharply increasing the gas pressure in the volume chamber 12 to an overshoot value $P_O$. As the gas flows through the tubing 14 and catheter 16 during interval $I_2$, the pressure in the volume chamber 12 drops and the balloon 18 becomes completely inflated at a steady-state pressure $P_I$. Intervals $I_1$ and $I_2$ combine as the inflation interval. At the beginning of active interval $I_3$, during which the gas pressure remains at $P_I$, the AP peaks again, at a pressure $AP_{I1}$, because of the balloon inflation. In the typical IABP, the pressure $AP_{I2}$ is the AP with the balloon 18 inflated, typically about 70 to 100 millimeters of mercury (mmHg) above atmospheric pressure and is close to $P_I$, the inflated gas pressure of the balloon 18. To begin interval $I_4$, the diaphragm 24 moves abruptly backward and the pressure drops abruptly to a partial vacuum $P_U$. During interval $I_5$, the gas in the balloon 18 flows through the catheter 16 and tubing 14 back into the volume chamber 12 and causing the AP to decrease. Intervals $I_4$ and $I_5$ combine as the deflation interval. Finally, during inactive interval $I_6$, the balloon has been completely deflated and gas pressure returns to the steady-state value $P_F$. Also at the beginning of $I_6$, the AP reaches its minimum, the diastolic point $AP_D$, and begins to rise to $AP_S$, ejecting blood to the aorta.

As the gas moves from the balloon 18 into the volume chamber 12 during $I_5$, the pressure gradient across the tubing 14 and catheter 16 decreases. With a decrease in the gradient also comes a decrease in the rate at which the balloon deflates. In other words, the balloon 18 deflates more slowly as it deflates. For example, using values for a typical system where $P_F$=10 mmHg, $AP_D$=50 mmHg, $P_U$=−200 mmHg, and $AP_I$=90 mmHg, all relative to atmospheric pressure, the pressure gradient drops from 290 mmHg at the beginning of $I_5$ to 40 mmHg at the end of $I_5$.

Figure 3:
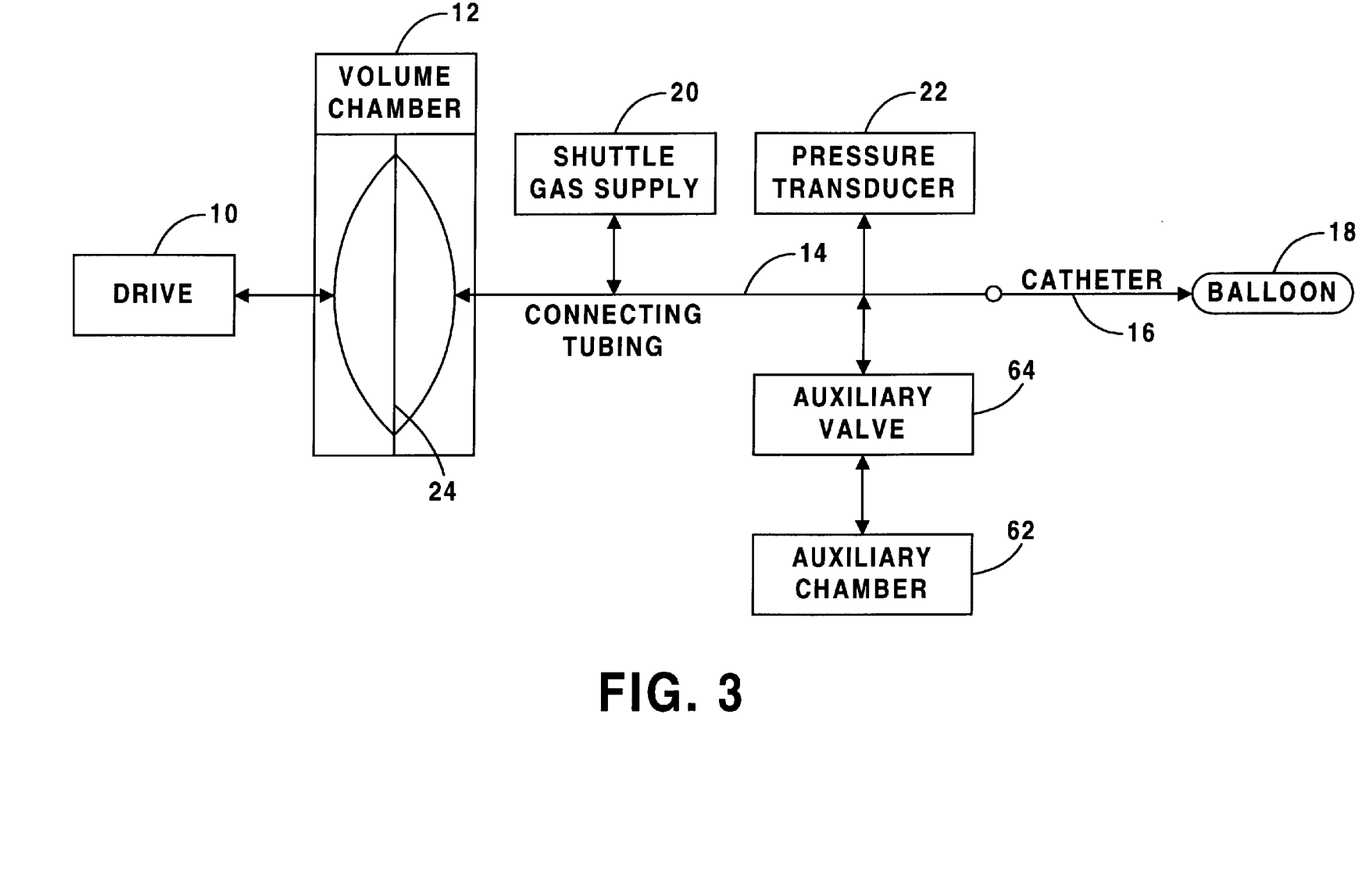
FIG. 3 shows a block diagram of an IABP employing the present invention.

The present invention includes a method for lowering the deflation time of the balloon while using a fill pressure $P_F$ at or slightly above atmospheric pressure, rather than the below atmospheric pressure used in IABPs of the prior art to augment the deflation rate, as described above. The main goal of the present invention is to increase the gradient across the tubing and catheter over that of the prior art during the deflation time. This is accomplished by removing a portion of the gas from the system during inflation and then restoring it into the system at or near the end of deflation. As shown in FIG. 3, the method utilizes a second volume chamber 62, or auxiliary chamber, that is connected to the system proximate to the volume chamber 12 by means of a bi-directional auxiliary valve 64. The auxiliary valve 64 is controlled to allow gas to flow into the auxiliary chamber 62 from the main portion of the system and to restore the gas to the system from the auxiliary chamber 62 at predetermined points in the inflation/deflation cycle, as described below.

Figure 4:
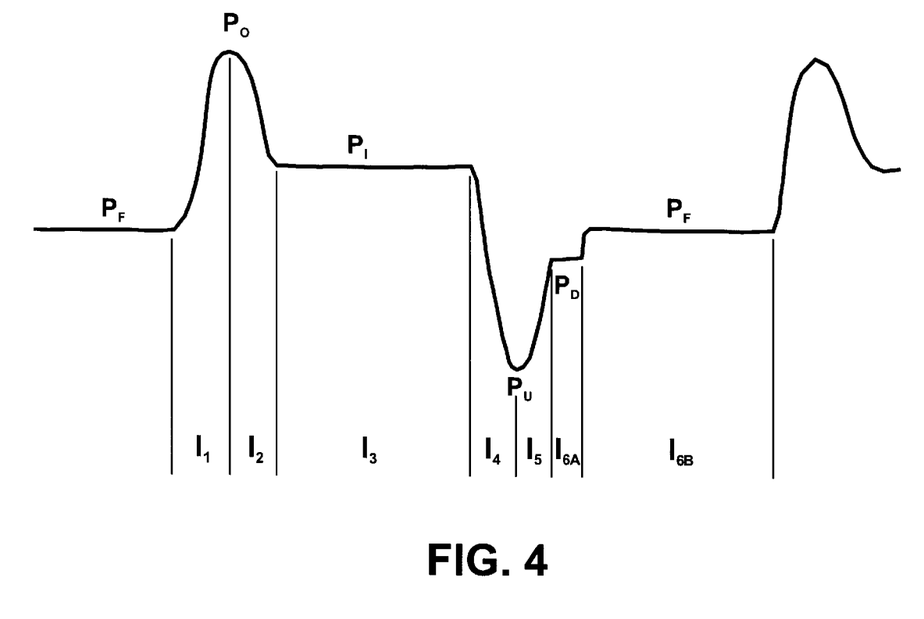
FIG. 4 shows a graph of gas pressure versus time for an IABP employing the present invention.

Referring to FIG. 4, sometime during $I_6$ of the previous cycle or during $I_1$, $I_2$, or $I_3$ of the current cycle, the auxiliary valve 64 is opened and gas flows into the auxiliary chamber 62. The exact point in the cycle at which the auxiliary valve 64 opens is not critical. It may have been left open from the previous cycle, as described below, or may be opened during the current cycle. When the gas pressure reaches a predetermined level, the auxiliary valve 64 is closed, leaving less gas in the main portion of the system, and resulting in the auxiliary chamber 62 being filled with gas at a pressure of $P_{AUX}$. The predetermined pressure level can be any level that causes $P_{AUX}$ to be greater than $P_F$, which means the auxiliary valve 64 can be closed at any point during $I_1$, $I_2$, or $I_3$. The preferred level for $P_{AUX}$ is when the gas pressure peaks at $P_O$. This is when the maximum amount of gas is in the auxiliary chamber 62 (the maximum amount of gas is removed from the main portion of the system), and the higher the gas pressure is in the auxiliary chamber 62, the smaller the auxiliary chamber 62 needs to be to hold a given amount of gas.

The amount of gas in the main portion of the system remains reduced as the cycle enters $I_5$. The reduction in the amount of gas enhances the partial vacuum $P_U$ produced by the volume chamber 12 during $I_5$. Enhancing the partial vacuum increases the pressure gradient across the tubing 14 and catheter 16, increasing the speed at which the gas flows from the balloon 18, and producing more rapid deflation. When the balloon 18 is deflated, the pressure in the volume chamber $P_D$ is lower than the fill pressure $P_F$ by the amount equal to the vacuum enhancement amount. Approximately at the end of $I_5$, when the balloon 18 has been substantially deflated, the auxiliary valve 64 is opened to readmitted the gas from the auxiliary chamber 62 into the system.

To determine the amount by which the present invention enhances the vacuum, the starting point is Boyle's law, which states that if the mass and absolute temperature of a gas are held constant, the product of its absolute pressure and volume is equal to a constant. Since the present invention is a closed system and assuming that the temperature of the gas remains essentially constant, the pressure-volume (PV) product at any two points in the cycle will be equal. Thus, in order to determine the increase in vacuum facilitated by the auxiliary chamber 62, the PV of the system before inflation is equated to the PV of the system just before opening the auxiliary valve to readmit gas to the system:

$$P_F(V_{NC}+V_D+V_A)=P_D(V_{NC}+V_D)+P_{AUX}V_A \qquad (1)$$

where $V_{NC}$ is the volume chamber volume, $V_D$ is the dead volume of the connecting tubing 14 and catheter 16, and $V_A$ is the auxiliary chamber volume. Also, it is assumed that the auxiliary valve 64 was closed when the pressure in the auxiliary chamber 62 was $P_O$ so that $P_{AUX}=P_O$. Solving for $P_F-P_D$, which represents the increased vacuum produced by temporarily storing gas in the auxiliary chamber 62, yields $$P_F-P_D=((P_O-P_F)\ V_A)/(V_{NC}+V_D) \qquad (2)$$

All of the above values are known relative to IABPs of the prior art except for the volume chamber volume $V_{NC}$. In order to determine the volume chamber volume, PV before inflation is set equal to PV after inflation:

$$P_F(V_{NC}+V_D+V_A)=P_I(V_D+V_B)+P_OV_A \qquad (3)$$

where $V_B$ is the balloon volume and it is assumed the auxiliary chamber is initially filled to pressure $P_F$ with the rest of the system. Solving for $V_{NC}$ yields $$V_{NC}=(P_I/P_F)(V_D+V_B)-V_D+((P_O-P_F)/P_F)V_A \qquad (4)$$

Substituting equation (4) into equation (2) results in $$P_F-P_D=((P_O-P_F)V_A)/((P_I/P_F)(V_D+V_B)+((P_O-P_F)/P_F)V_A) \qquad (5)$$

The addition of the auxiliary chamber 62 is not the only modification that is made in the method of the present invention. In order to fully inflate the balloon after gas has been removed into the auxiliary chamber, there must be a greater amount of gas in the system while the system pressures remain the same. Consequently, the volume of the volume chamber is greater in the system of the present invention. In prior art IABPs, the system volume before inflation is the sum of the prior art chamber volume $V_{PC}$ and the dead volume of the tubing and catheter $V_D$, which are at pressure $P_F$. After inflation, the system volume is the sum of the dead volume $V_D$ and the balloon volume $V_B$, which are at pressure $P_I$. Boyle's law yields the equation $$P_F(V_{PC}+V_D)=P_I(V_D+V_B) \qquad (6)$$

and solving for $V_{PC}$ yields $$V_{PC}=(P_I/P_F)(V_D+V_B)-V_D \qquad (7)$$

Note that the first two terms on the right side of equation (4) are the same as the right side of equation (7). Thus, equation (7) becomes $$V_{NC}=V_{PC}+((P_O-P_F)/P_F))V_A \qquad (8)$$

In order to see how much the present invention improves performance of an IABP, typical numbers for pressures and volumes are inserted into the above equations. It is also assumed that the atmospheric pressure is standard atmospheric pressure at sea level, which is 760 mmHg. The absolute pressures used here for typical numbers will change as local atmospheric pressure changes and pressures relative to local atmospheric pressure are shown in parenthesis. The initial fill pressure $P_F$ is preferably in the range of from 760 to 775 mmHg (0 to 15 mmHg above local atmospheric pressure). As discussed above, it is preferable to keep the fill pressure at or above atmospheric because of the advantages in leak detection, simplicity in filling apparatus, and emergency operation. However, the fill pressure must be lower than the lowest AP, which is about 800 to 820 mmHg (40 to 60 mmHg) for the typical IABP patient, otherwise the balloon will not empty completely. A typical fill pressure is 770 mmHg (10 mmHg).

The inflated pressure $P_I$ is the same as the AP during the period of time that the balloon is inflated, which is generally in the range of from 830 to 860 mmHg (70 to 100 mmHg). A typical value is 850 mmHg (90 mmHg).

A wide range of pressures are usable for the overshoot pressure $P_O$. $P_O$ is a function of, among other things, how fast the diaphragm 24 pushes forward during $I_1$. Preferably, $P_O$ will be in the range of from 860 to 1160 mmHg (100 to 400 mmHg). A typical value is 1010 mmHg (250 mmHg).

Like the overshoot pressure $P_O$, a wide range of pressures are usable for the undershoot pressure $P_U$. $P_U$ is a function of, among other things, how fast the diaphragm 24 pulls backward during $I_4$. Preferably, $P_U$ will be in the range of from 460 to 660 mmHg (−300 to −100 mmHg). A typical value is 560 mmHg (−200 mmHg).

There are a variety of IABP balloons known in the art, all of which can be used with the present invention. They all have the same basic tubular shape, although some are tapered or have other shapes that vary from cylindrical. The typical cylindrical balloon has an average diameter of about 1.9 centimeters (cm) and a length of about 14 cm when inflated, for a volume $V_B$ of about 40 cm³.

The dead volume $V_D$ is the sum of the volumes of the connecting tubing and the catheter. The dead volume can vary considerably from system design to system design, but a typical value is 35 cm³, which is from a tubing/catheter combination that is about 180 cm long and that has an average inside diameter of about 0.5 cm.

The purpose of the auxiliary chamber is to temporarily remove some of the gas from the system. Theoretically, the volume of the auxiliary chamber has no limit because, regardless of the volume, at least some gas will be removed from the system. There are practical considerations, however. The amount of gas removed from the system by the auxiliary chamber determines how much the present invention improves performance of the IABP. Therefore, the lower limit of the auxiliary chamber volume is dictated by the minimum amount of performance enhancement desired. The lower limit depends upon other parameters of the system, such as the total volume of the system, the gas pressures involved, etc. For a typical system, a practical lower limit is 5 cm³. The upper limit has more to do with the physical size of the system, and so is dictated by space and portability considerations. A typical range of values for $V_A$ is from 15 to 50 cm³, where 20 cm³ is used as a typical value throughout the remainder of this specification.

Substituting the above pressure and volume values into equation (5) yields $$P_F - P_D = ((1010-770)20)/ \qquad (9)$$
$$((850/770)(35+40) + ((1010-770)/770)20)$$
$$= 54 \text{ mmHg}$$

Thus, for the given values of pressure and volume, the vacuum is enhanced during deflation by 54 mmHg. This means that the pressure gradient from the volume chamber to the balloon at the end of deflation is 94 mmHg, more than double the typical 40 mmHg of IABPs of the prior art. Substituting different values for the system parameters yield different results. For example, if the overshoot pressure $P_O$ is 1110 mmHg (350 mmHg), the vacuum enhancement is 74 mmHg, for an end-of-deflation gradient of 114 mmHg, almost three times that of the prior art IABPs.

Note that the amount by which the vacuum is enhanced is not proportional to the pressure gradient, but is an absolute amount. Consequently, the enhancement has a much more profound effect at the end of deflation, where it is more needed, than at the beginning of deflation, where the pressure gradient is already large. The effect is most readily seen in the last 20% of deflation. Table I shows, using experimental data, how IABP performance is improved by the method of the present invention with above typical values. Naturally, the improvement will vary with the system parameters.

TABLE I

|  | Full deflation 100%–0% | Final 20% 20%–0% |
|---|---|---|
| Prior art IABP | 190 ms | 80 ms |
| Present IABP | 140 ms | 45 ms |

The increase in the size of the volume chamber from that of the prior art is determined from equation (8). Substituting the above values yields $$V_{NC} = V_{PC} + ((1010-770)/770))20 \qquad (10)$$
$$= V_{PC} + 6.2 \text{ cm}^3$$

In order to perceive the magnitude of increase, the volume of a prior art volume chamber is determined by equation (7) as $$V_{PC} = (850/770)(35+40) - 35 \qquad (11)$$
$$= 47.8 \text{ cm}^3$$

Thus, the volume chamber of the present invention is only 13% larger than the volume chamber of the prior art.

Thus it has been shown and described a method and apparatus for improved IABP deflation time which satisfies the objects set forth above.

Since certain changes may be made in the present disclosure without departing from the scope of the present invention, it is intended that all matter described in the foregoing specification and shown in the accompanying drawings be interpreted as illustrative and not in a limiting sense.

What is claimed is:

1. A method for decreasing the deflation time of the balloon of an intra-aortic balloon pump assembly, said assembly including a main pneumatic system for inflating and deflating said balloon with a gas during a repetitive cycle, said main pneumatic system including a volume chamber in pneumatic communication with one end of a catheter and said balloon in pneumatic communication with another end of said catheter, said volume chamber having a gas pressure, said catheter having a gas pressure gradient between said volume chamber and said balloon, said method comprising the steps of:

(a) inflating said balloon during an inflation interval;
   (b) maintaining said balloon at an inflation pressure during an active interval;
   (c) removing a portion of said gas from said main pneumatic system during said inflation interval or said active interval;
   (d) deflating said balloon during a deflation interval;
   (e) restoring said portion of said gas to said main pneumatic system at approximately the end of said deflation interval; and
   (f) maintaining said balloon at a deflation pressure during an inactive interval;

(g) whereby said removing said portion of said gas increases said gas pressure gradient during said deflation interval compared to an assemblage not implementing said method, causing a faster gas flow from said balloon to said volume chamber during said deflation interval, and decreasing deflation time.

2. The method of claim 1 wherein said removing step occurs during said inflation interval.

3. The method of claim 1 wherein said restoring step occurs at substantially the end of said deflation interval.

4. The method of claim 1 wherein said volume chamber gas pressure during said inactive interval is within approximately 15 mmHg of atmospheric pressure.

5. The method of claim 1 wherein said removing step and restoring step occur at a point physically proximate to said volume chamber.

6. The method of claim 1 wherein said assemblage includes an auxiliary chamber in pneumatic communication with said main pneumatic system for storing said portion of said gas between said removing step and said restoring step.

7. The method of claim 6 wherein an auxiliary valve is in pneumatic communication with and between said auxiliary chamber and said main pneumatic system proximate to said volume chamber, said auxiliary valve closing to perform said removing step, remaining closed to perform said storing step, and opening to perform said restoring step.

8. The method of claim 7 wherein said closing of said auxiliary valve occurs during said inflation interval.

9. The method of claim 7 wherein said opening of said auxiliary valve occurs at substantially the end of said deflation interval.

10. A method for decreasing the deflation time of the balloon of an intra-aortic balloon pump assembly, said assembly including a main pneumatic system for inflating and deflating said balloon with a gas during a repetitive cycle, said main pneumatic system including a volume chamber in pneumatic communication with one end of a catheter and said balloon in pneumatic communication with another end of said catheter, said volume chamber having a gas pressure, said catheter having a gas pressure gradient between said volume chamber and said balloon, said method comprising the steps of:

(a) inflating said balloon during an inflation interval;

(b) removing a portion of said gas from said main pneumatic system at a point physically proximate to said volume chamber during said inflation interval;

(c) maintaining said balloon at an inflation pressure during an active interval;

(d) deflating said balloon during a deflation interval;

(e) restoring said portion of said gas to said main pneumatic system at a point physically proximate to said volume chamber at substantially the end of said deflation interval; and (f) maintaining said balloon at a deflation pressure that is within approximately 15 mmHg of atmospheric pressure during an inactive interval;

(g) whereby said removing said portion of said gas increases said gas pressure gradient during said deflation interval compared to an assemblage not implementing said method, causing a faster gas flow from said balloon to said volume chamber during said deflation interval, and decreasing deflation time.

11. The method of claim 10 wherein said assemblage includes an auxiliary valve in pneumatic communication with said main pneumatic system proximate to said volume chamber and an auxiliary chamber in pneumatic communication with said auxiliary valve, said auxiliary chamber storing said portion of said gas between said removing step and said restoring step, said auxiliary valve closing to perform said removing step, remaining closed to perform said storing step, and opening to perform said restoring step.

12. An intra-aortic balloon pump assembly comprising:

(a) a main pneumatic system including a volume chamber, a catheter, and an intra-aortic balloon;

(b) said volume chamber having a volume and a means for changing said volume, said volume chamber being in pneumatic communication with an end of said catheter;

(c) said balloon being in pneumatic communication with another end of said catheter;

(d) an auxiliary chamber in pneumatic communication with an auxiliary valve, said auxiliary valve being in pneumatic communication with said main pneumatic system proximate to said volume chamber;

(e) control means for controlling said volume chamber volume and said auxiliary valve during a repetitive cycle, said cycle including an inflation interval when said balloon is inflating, an active interval when said balloon is inflated, a deflation interval when said balloon is deflating, and an inactive interval when said balloon is deflated;

(f) gas supply means in pneumatic communication with said main pneumatic system for supplying said main pneumatic system with gas such that main pneumatic system gas pressure is at a predetermined gas pressure during said inactive interval; and (g) said control means closing said auxiliary valve during said inflation interval or said active interval so that a portion of said gas is removed from said main pneumatic system and opening said auxiliary valve at approximately the end of said deflation interval to restore said portion of said gas to said main pneumatic system.

13. The assemblage of claim 12 wherein said control means closes said auxiliary valve during said inflation interval.

14. The assemblage of claim 12 wherein said control means opens said auxiliary valve at substantially the end of said deflation interval.

15. The assemblage of claim 12 wherein said predetermined gas pressure is within approximately 15 mmHg of atmospheric pressure.

16. An intra-aortic balloon pump assembly comprising:

(a) a main pneumatic system including a volume chamber, a catheter, and an intra-aortic balloon;

(b) said volume chamber having a volume and a means for changing said volume, said volume chamber being in pneumatic communication with an end of said catheter;

(c) said balloon being in pneumatic communication with another end of said catheter;

(d) an auxiliary chamber in pneumatic communication with an auxiliary valve, said auxiliary valve being in pneumatic communication with said main pneumatic system proximate to said volume chamber;

(e) control means for controlling said volume chamber volume and said auxiliary valve during a repetitive cycle, said cycle including an inflation interval when said balloon is inflating, an active interval when said balloon is inflated, a deflation interval when said balloon is deflating, and an inactive interval when said balloon is deflated;

(f) gas supply means in pneumatic communication with said main pneumatic system for supplying said main pneumatic system with a gas such that main pneumatic system gas pressure is within approximately 15 mmHg of atmospheric pressure during said inactive interval; and (g) said control means closing said auxiliary valve during said inflation interval so that a portion of said gas is removed from said main pneumatic system and opening said auxiliary valve at substantially the end of said deflation interval to restore said portion of said gas to said main pneumatic system.

* * * * *